United States Patent [19]

Uhari et al.

[11] Patent Number: 5,719,196
[45] Date of Patent: Feb. 17, 1998

[54] METHOD OF TREATING RESPIRATORY INFECTIONS OR COMPLICATIONS DERIVED THEREFROM IN HUMANS WHICH INCLUDES ORAL ADMINISTRATION OF XYLITOL

[75] Inventors: Matti Kalervo Uhari; Tero Tapani Kontiokari, both of Oulu, Finland

[73] Assignee: Leiras Oy, Turku, Finland

[21] Appl. No.: 685,506

[22] Filed: Jul. 24, 1996

[51] Int. Cl.⁶ .................................................. A61K 31/045
[52] U.S. Cl. ............................................................. 514/738
[58] Field of Search ............................................. 514/738

[56] References Cited

PUBLICATIONS

Kontiokari et al., "Effect of Xylitol on Growth of Nasopharyngeal Bacteria in Vitro," Antimicrobial Agents and Chemotherapy, vol. 9, No. 8, Aug., 1995, pp. 1820–1823.

*Primary Examiner*—Rebecca Cook
*Attorney, Agent, or Firm*—Adduci, Mastriani & Schaumberg, L.L.P.

[57] ABSTRACT

A new use of xylitol is disclosed. The invention relates to a method of treating respiratory infections, especially acute otitis media, in humans which method comprises oraly administering to the human an effective amount of xylitol.

10 Claims, 1 Drawing Sheet

5,719,196

1

METHOD OF TREATING RESPIRATORY INFECTIONS OR COMPLICATIONS DERIVED THEREFROM IN HUMANS WHICH INCLUDES ORAL ADMINISTRATION OF XYLITOL

FIELD OF THE INVENTION

The present invention relates to a means of treating respiratory infections in humans, and, more particularly, to a method of preventing acute otitis media involving oral administration of xylitol.

BACKGROUND OF THE INVENTION

Xylitol has been classified as a polyol or a sugar alcohol and is referred to as birch sugar, because it can be produced from birch. Xylitol occurs widely in nature, although the concentrations are low. Natural sources of xylitol include plums, strawberries, rasberries and rowan berries.[1] Xylitol has the same relative sweetness as sucrose, and it has been used as a sugar substitute for dietary and medical purposes. Because of its five-carbon sugar alcohol structure, xylitol is unsuitable as a source of energy for most oral microorganisms, such as Streptococcus mutans.[2] Yet, most S. mutans strains are, via the fructose phospho-transferase system, able to transport xylitol into the cell, where it is phosphorylated into xylitol-5-phosphate, which then has to be expelled from the cell.[3] This metabolically futile xylitol cycle consumes energy stores of the cell and is thought to be responsible for the inhibition of the growth of S. mutans observed both in vitro and in vivo when exposed to xylitol.[4]

Regular consumption of xylitol has been shown to reduce the incidence of dental caries, although the mechanisms are not completely understood.[5–8] The most significant effect so far demonstrated is the ability of xylitol to reduce the growth and acid production of S. mutans, which is the most important bacterium taking part in the pathomechanism of dental caries.[9]

We have previously found that xylitol inhibits the growth of S. pneumonine and S. mutans in vitro during their logarithmic growth phase. This effect is dose-dependent. We similarly observed a slight postexponential inhibition of growth with beta-hemolytic streptococci, but not with Haemophilus influenzae, nor with Moraxella catarrhalis.[10] The disclosure of this reference 10 is hereby incorporated as reference. S. pheumoniae is an important etiologic agent of bacterial pneumonia, sepsis and meningitis.[11] It accounts for about 30% of all acute otitis media (AOM) episodes, as estimated by bacterial cultures from the middle-ear.[12–13] This figure may be even higher when more sensitive methods of detecting bacteria are applied.[14] At the age of 3 years, 20 to 40% of healthy children carry pneumococci in their nasopharynx. This carriage increases during acute infections.[15] Nasopharyngeal carriage of pneumococci has been shown to be a predisposing factor for AOM in children in the day care setting.[15]

SUMMARY OF THE INVENTION

The present invention relates to the use of xylitol for the treatment of respiratory infections, especially acute otitis media, in humans. The present invention is based on the surprising discovery that xylitol exhibits a growth inhibiting effect against pneumococci which reduces the pneumococcal carriage rates and also reduces the incidence of acute otitis media.

2

DETAILED DESCRIPTION OF THE INVENTION

Figure 1:
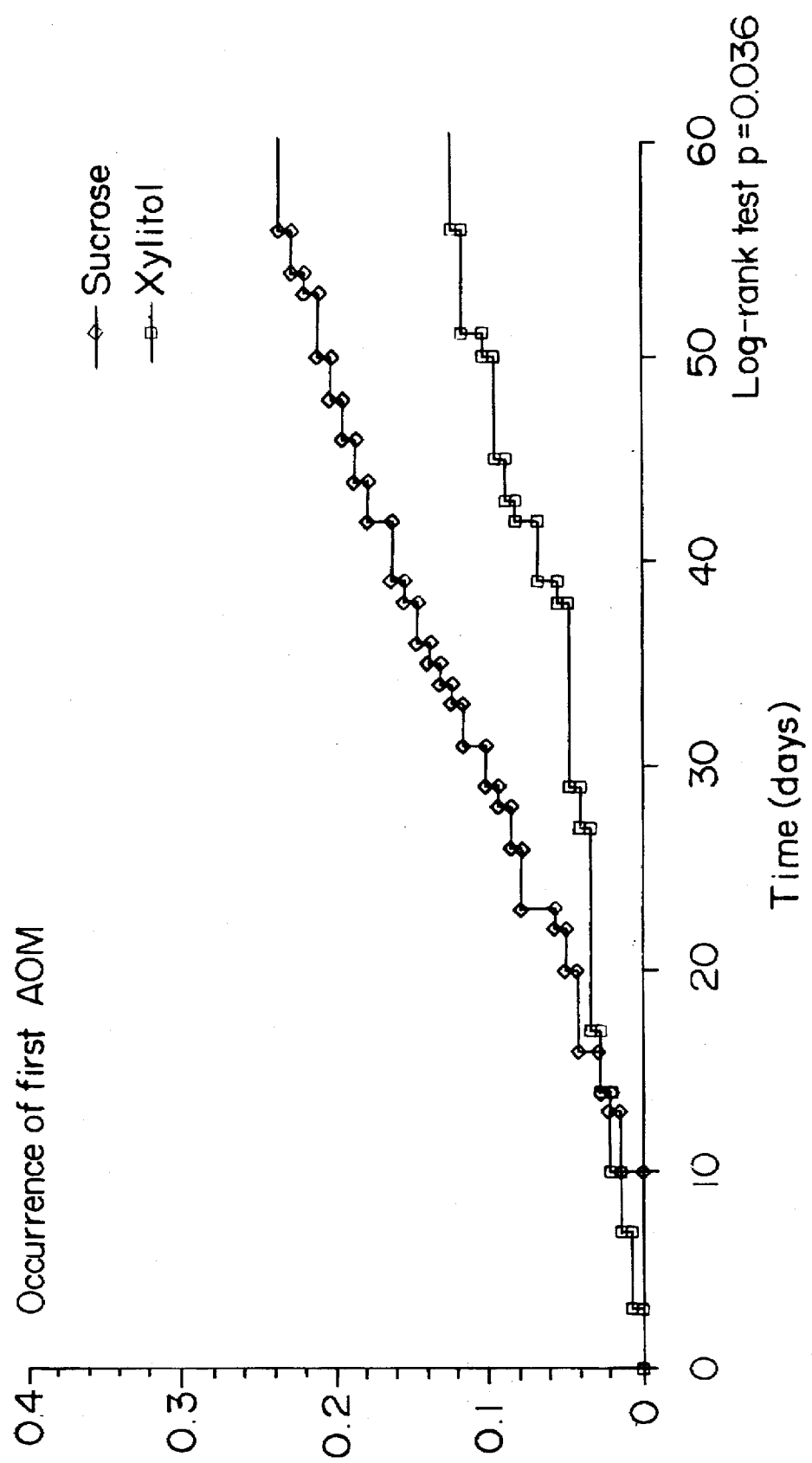
FIG. 1 shows graphically the cumulative occurrence of first acute otitis media (AOM) attack during a two-month monitoring period in a xylitol group and a reference sucrose group.

In accordance with the present invention there is provided a method of treating respiratory infections in humans which comprises orally administering to the human an effective amount of xylitol.

As used herein respiratory infections include acute otitis media (AOM), upper respiratory infection, acute bronchitis, sinusitis and conjunctivitis.

According to a preferred embodiment of the invention there is provided a method of preventing acute otitis media in humans which comprises orally administering to the human an effective amount of xylitol.

The xylitol may be formulated as a solid or liquid preparation.

The solid preparation may be in the form of, for example, tablets, powders or lozenges or chewing gums, and may contain conventional excipients and fillers.

The liquid preparation may be in the form of, for example, an aqueous solution or syrup, and may contain conventional additives.

The suitable daily dose of the xylitol may vary widely depending on, for example, the administration form, the age and condition of the human being subjected to the treatment. A suitable daily dose for children by using xylitol chewing gums may range from about 6 grams to about 10 grams, especially from about 8 grams to about 9 grams.

PHARMACOLOGY

Our hypothesis that the growth inhibiting effect of xylitol against pneumococci could reduce the pneumococcal carriage rates and also reduce the incidence of AOM, was evaluated in a double-blind randomized trial using chewing gum as the vehicle to deliver xylitol to children.

METHODS

Study Design

The study was a randomized double-blind trial performed in 11 day care centers in the city of Oulu. The study protocol was evaluated and approved by the Ethical Committee of the Health Center of Oulu. The parents of the participating children gave informed consent. The study material was donated by Leaf-Huhtamäki (Leaf-Huhtamäki Co., Turku, Finland) and was sent to us packaged in number coded cartridges containing 60 numbered boxes with 10 pieces of chewing gum, each sweetened with either xylitol or sucrose according to a random sequence produced using a random number table. To ensure equal numbers of children in the sucrose and xylitol groups in each of the day care centers, we used block randomization with a block size of four.[16] The children were numbered in the order they entered the study and each child received one cartridge according to his/her number and was instructed to chew two pieces 5 times (one box) per day after meals, making a total dose of 8.4 g xylitol per day. The chewing lasted until there was no taste left or at least 5 minutes. The parents were asked to proceed with the normal feeding routines, but to avoid the use of xylitol during the study. If dental caries was noticed while taking the nasopharyngeal samples, the child was advised not to participate in the study because of the sucrose content of the placebo chewing gum.

RESULTS

A total of 336 children were enrolled in March 1995. There were 30 drop-outs, which left 306 children, 149 in the sucrose group and 157 in the xylitol group, eligible for analysis. The restfits obtained are summarized in Table 1.

TABLE 1

Respiratory infections recorded by the treating physician

| Diagnose | Sucrose (n = 149) Number | Xylitol (n = 157) | P-value* |
|---|---|---|---|
| Acute otatis media** | 43 | 22 | 0.033 |
| Upper respiratory infection | 14 | 11 | 0.33 |
| Acute bronchitis | 5 | 2 | 0.37 |
| Sinusitis | 2 | 3 | 0.70 |
| Conjuctivitis | 3 | 1 | 0.29 |

*Man-Whitney U-test
**Number of the children with at least one event of AOM was 31 in sucrose vs. 19 in xylitol group, 8.7% difference with 95% CI 0.4–17.0% (p < 0.04).

The numbers of upper respiratory tract infections, acute bronchitis, sinusitis and conjunctivitis leading to visits to 41 different physicians were somewhat smaller in the xylitol group than in the sucrose group. The total number of AOM attacks was 43/149 among the children in the sucrose group as compared to 22/157 among the children who received xylitol. The number of children with at least one episode of AOM was 31/149 (20.8%) in the sucrose group and 19/157 (12.1%) among those who received xylitol (difference 8.7%, 95% CI 0.4–17.0%, p=0.040). The occurrence of the first AOM attack differed significantly between the groups when tested with the log-rank test (p=0.036) (FIG. 1) and was associated with the amount of xylitol used: those who experienced AOM had forgotten their xylitol chewing gums significantly more often than those who had not had any AOM events, the means of forgotten xylitol being 48.8 g vs. 22.4 g (difference 26.4 g, 95% CI 5.7–47.1 g, p=0.024), respectively. Within the sucrose group, there was no significant association between the occurrence of AOM and the use of sucrose chewing gums, and the mean amount of gum forgotten by those with AOM was 25.9 g as compared to 28.0 g of those who had not had any AOM attacks (difference −2.2 g, 95% CI −27.0 −22.7 g, p=0.68).

The total number of antimicrobial medications prescribed in the xylitol group was 34 as compared to 60 in the control group. At least one period of antimicrobials was received by 43/149 (28.9%) children in the sucrose group and 29/157 (18.5%) children in the xylitol group (difference 10.4% with 95% CI for the difference 0.9%–19.9%, p=0.032).

All the possible the risk factors of AOM, i.e. parental education and smoking, breast feeding, use of pacifier, otitis-prone sibling, previous history of AOM, previous use of xylitol, and nasopharyngeal carriage of pneumococci were controlled using a logistic multivariate analysis. When at least one attack of AOM was the dependent variable of the model, the type of sugar given to the child significantly associated with the occurrence of AOM in such a way that the children receiving xylitol had fewer attacks of AOM (p=0.045).

Two children in our trial stopped the use of xylitol because of complaints of diarrhea. Yet, the recorded number of diarrhea episodes and the mean duration of diarrhea were similar in the xylitol and sucrose groups. The dose of 8.4 g xylitol used in our trial is markedly less than the maximal dose previously reported to be tolerable.[17]

Respiratory infections, and especially AOM, in children are the main reason for the use of oral antimicrobials.[18] The emergence of multi-drag resistant strains of S. pneumoniae substantiates the need for new approaches in preventing bacterial infections. We have been able to show that xylitol, a well-tolerated food additive, is effective in preventing AOM in children.

LIST OF REFERENCES

1. Mäkinen K K., Söderling E. A quantitative study of mannitol, sorbitol, xylitol, and xylose in wild berries and commercial fruits. J. Food Sci. 1980;45:367–71.

2. Knuuttila MLE., Mäkinen K K. Effect of xylitol on the growth and metabolism of Streptococcus mutans. Caries Res. 1975;9: 177–89.

3. Assev S., Rölla G. Evidence for presence of the xylitol phosphotransferase system in Streptococcus mutans OMZ 176 by xylitol. Acta Pathol Microbiol Immunol Scand B 1984;92:89–92.

4. Söderling E., Pihlanto-Leppälä A. Uptake and expulsion of 14C-xylitol by xylitol-cultured Streptococcus mutans ATCC 25175 in vitro. Scand. J. Dent. Res. 1989;97:511–9.

5. Scheinin A., Mäkinen KK. Turlm sugar studies I-XXI. Acta Odontol Scand. 1975;33 :Suppl 70:1–351.

6. Scheinin A., Bánóczy J. Xylitol and caries: The collaborative WHO oral disease preventive program in Hungary. Int. Dent. J. 1985;35:50–7.

7. Isokangas P., Alanen P., Tiekso J., Mäkinen K K. Xylitol chewing gum in caries prevention. A field Study in children. J. Am. Dent. Assoc. 1988;117:315–20.

8. Kandelman D., Bär A., Hefti A. Collaborative WHO xylitol field study in French Polynesia. Caries Res. 1988;22:55–62.

9. Vadeboncoeur C., Trahan L., Mouton C., Mayrand D. Effect of xylitol on the growth and glycolysis of acidogenic oral bacteria. J. Dent. Res. 1983;62:882–4.

10. Kontiokad T., Uhad M., Koskela M. Effect of xylitol on growth of nasopharyngeal bacteria in vitro. Anfimicrob Agents Chemother 1995;39:1820–3.

11. Bruyn GAW., Zegers BJM., van Furth R. Mechanisms of host defense against infection with streptococcus pneumoniae. Clin. Infect Dis. 1992;14:251–62.

12. Luotonen J., Herva E., Karma P., Timonen M., Leinonen M., Mäkelä PH. The bacteriology of acute otitis media in children with special reference to streptococcus pneumoniae as studied by bacteriological and antigen detection methods. Scand. J. Infect Dis. 1981;13:177–83.

13. Harrison C J., Chartstrand S A., Pichichero M E. Microbiologic and clinical aspects of a trial of once daily cefixime compared with twice daily cefaclor for treatment of acute otitis media in infants and children. Pediatr. Infect Dis. J. 1993;12:62–9.

14. Del Beccaro M A., Mendelman P M., Inglis A F. et al. Bacteriology of acute otitis media: A new perspective. J. Pediatr. 1992; 120:81–4.

15. Faden H., Waz M J., Bernstein Jm., Brodsky L., Stanievich J., Ogra P L. Nasopharyngeal flora in the first three years of life in normal and otitis-prone children. Ann. Otol. Rhinol. Laryngol 1991; 100:612–5.

16. Pocock, S J. Clinical trials. A practical approach. Chichester: John Wiley & Sons; 1983.

17. Åkerblom H K., Koivukangas K T., Puukka R., Mononen M. The tolerance of increasing amounts of dietary xylitol in ckildren. Int. J. Vitam. Nutr. Res. 1982;22:53–66.

18. Berman S. Otitis media in children. N. Engl. J. Med. 1995; 332: 1560–5.

What is claimed is:

1. A method of treating an infection in a human in need of said treatment which comprises orally administering to the human an effective amount of xylitol, wherein said infection is selected from the group consisting of acute otitis media, upper respiratory infection, acute bronchitis, sinusitis and conjunctivitis.

2. The method of claim 1 in which the infection is acute otitis media.

3. The method of claim 1, wherein the infection is conjunctivitis.

4. The method of claim 1 wherein xylitol is orally administered in the form of a solid preparation.

5. The method of claim 4 wherein the orally administered form comprises chewing gum.

6. The method of claim 1 wherein xylitol is orally administered in the form of a liquid preparation.

7. The method of claim 1 wherein xylitol is administrated in a daily dosage range of between 6 grams and 10 grams.

8. A method of treating acute otitis media in a human in need of said treatment which comprises orally administering to the human an effective amount of xylitol in the form of a chewing gum.

9. The method of claim 8 wherein xylitol is administrated in a daily dosage range of between 6 grams and 10 grams.

10. The method of claim 9 wherein xylitol is administrated in a daily dosage range of between 8 grams and 9 grams.

* * * * *